United States Patent
Sliwa et al.

(10) Patent No.: US 9,138,148 B2
(45) Date of Patent: Sep. 22, 2015

(54) HIGH SPEED ELASTOGRAPHIC PROPERTY MAPPING OF LUMENS UTILIZING MICROPALPATION DELIVERED FROM AN OCT-EQUIPPED CATHETER TIP

(75) Inventors: John Sliwa, Los Altos Hills, CA (US); Yu Liu, Irvine, CA (US)

(73) Assignee: ST. JUDE MEDICAL, INC., St. Paul, MN (US)

( * ) Notice: Subject to any disclaimer, the term of this patent is extended or adjusted under 35 U.S.C. 154(b) by 0 days.

(21) Appl. No.: 13/285,167

(22) Filed: Oct. 31, 2011

(65) Prior Publication Data

US 2012/0265061 A1 Oct. 18, 2012

Related U.S. Application Data

(60) Provisional application No. 61/475,173, filed on Apr. 13, 2011.

(51) Int. Cl.
*A61B 5/05* (2006.01)
*A61B 5/00* (2006.01)
*A61B 5/02* (2006.01)
*A61M 25/00* (2006.01)

(52) U.S. Cl.
CPC .............. *A61B 5/0066* (2013.01); *A61B 5/0053* (2013.01); *A61B 5/02007* (2013.01); *A61M 25/007* (2013.01)

(58) Field of Classification Search
None
See application file for complete search history.

(56) References Cited

U.S. PATENT DOCUMENTS

| | | | |
|---|---|---|---|
| 5,324,260 A * | 6/1994 | O'Neill et al. | 604/103.08 |
| 5,524,636 A * | 6/1996 | Sarvazyan et al. | 600/587 |
| 5,749,364 A * | 5/1998 | Sliwa et al. | 600/438 |
| 5,836,896 A * | 11/1998 | Rosenschein | 601/2 |
| 6,445,944 B1 * | 9/2002 | Ostrovsky | 600/425 |
| 6,615,071 B1 * | 9/2003 | Casscells et al. | 600/474 |
| 6,702,776 B2 * | 3/2004 | Quinn | 604/43 |
| 7,344,528 B1 * | 3/2008 | Tu et al. | 606/7 |
| 7,538,859 B2 * | 5/2009 | Tearney et al. | 356/35.5 |
| 7,611,542 B2 * | 11/2009 | Bourne et al. | 623/23.72 |
| 7,725,169 B2 * | 5/2010 | Boppart et al. | 600/473 |
| 7,751,057 B2 * | 7/2010 | Oldenburg et al. | 356/497 |
| 7,753,926 B1 * | 7/2010 | Pacetti | 606/159 |
| 7,787,129 B2 * | 8/2010 | Zysk et al. | 356/481 |
| 7,809,428 B2 * | 10/2010 | Elmaleh et al. | 600/436 |

(Continued)

OTHER PUBLICATIONS

Kennedy et al, "In vivo three-dimensional optical coherence elastography", Mar. 28, 2011 / vol. 19, No. 7 / Optics Express 6623.*

(Continued)

*Primary Examiner* — Nicholas Evoy
(74) *Attorney, Agent, or Firm* — Mattingly & Malur, PC

(57) ABSTRACT

A method for performing elastographic deformation mapping of tissues and plaques comprises: introducing a distal portion of a catheter to an interior of an interior body of a patient; applying, from a palpator in the distal portion, one of a directed fluid or a mechanical indenter to produce a surface-applied palpation force to a target area of the interior body to mechanically displace the interior body and cause elastographic deformation of the target area of one or more surface and subsurface tissues and plaques; and directing and delivering an OCT (optical coherence tomography) beam, from an OCT imaging sensor in the distal portion, for OCT deformation detection including elastographic deformation measurement to provide elastographic mapping of the target area.

24 Claims, 4 Drawing Sheets

(56) References Cited

U.S. PATENT DOCUMENTS

| | | | |
|---|---|---|---|
| 7,999,945 B2 * | 8/2011 | Zara ............................. 356/479 |
| 8,002,771 B2 * | 8/2011 | Cox et al. ...................... 606/51 |
| 8,187,221 B2 * | 5/2012 | Bates ....................... 604/103.01 |
| 8,214,010 B2 * | 7/2012 | Courtney et al. ............ 600/407 |
| 8,457,715 B2 * | 6/2013 | McKenna et al. ............ 600/424 |
| 8,460,195 B2 * | 6/2013 | Courtney et al. ............ 600/463 |
| 8,517,962 B2 * | 8/2013 | Gertner et al. ................... 601/2 |
| 8,518,053 B2 * | 8/2013 | Tanaka et al. ................. 606/108 |
| 8,521,257 B2 * | 8/2013 | Whitcomb et al. ............ 600/411 |
| 8,537,203 B2 * | 9/2013 | Seibel et al. ..................... 348/45 |
| 8,582,934 B2 * | 11/2013 | Adler et al. ..................... 385/33 |
| 8,712,506 B2 * | 4/2014 | Courtney et al. ............ 600/478 |
| 8,784,321 B2 * | 7/2014 | Courtney et al. ............ 600/463 |
| 2002/0183601 A1 * | 12/2002 | Tearney et al. ............... 600/310 |
| 2003/0055307 A1 * | 3/2003 | Elmaleh et al. ................... 600/1 |
| 2003/0082105 A1 * | 5/2003 | Fischman et al. .............. 424/9.6 |
| 2004/0097805 A1 * | 5/2004 | Verard et al. .................. 600/428 |
| 2004/0143322 A1 * | 7/2004 | Litvack et al. ................ 623/1.42 |
| 2004/0199202 A1 * | 10/2004 | Dubrul et al. ................. 606/200 |
| 2005/0113811 A1 * | 5/2005 | Houser et al. ..................... 606/1 |
| 2005/0149002 A1 * | 7/2005 | Wang et al. ........................ 606/1 |
| 2005/0149169 A1 * | 7/2005 | Wang et al. ................... 623/1.15 |
| 2005/0165471 A1 * | 7/2005 | Wang et al. ................... 623/1.15 |
| 2006/0047263 A1 * | 3/2006 | Tu et al. .......................... 604/521 |
| 2006/0058592 A1 * | 3/2006 | Bouma et al. ................. 600/301 |
| 2006/0064009 A1 * | 3/2006 | Webler et al. ................. 600/434 |
| 2006/0189928 A1 * | 8/2006 | Camus et al. ............ 604/101.01 |
| 2006/0265043 A1 * | 11/2006 | Mandrusov et al. ......... 623/1.11 |
| 2007/0010702 A1 * | 1/2007 | Wang et al. ......................... 600/8 |
| 2007/0258906 A1 * | 11/2007 | Fischman et al. ............ 424/9.71 |
| 2008/0033297 A1 * | 2/2008 | Sliwa ............................. 600/439 |
| 2008/0177138 A1 * | 7/2008 | Courtney et al. ............ 600/109 |
| 2008/0177139 A1 * | 7/2008 | Courtney et al. ............ 600/109 |
| 2008/0177183 A1 * | 7/2008 | Courtney et al. ............ 600/463 |
| 2008/0319375 A1 * | 12/2008 | Hardy ............................. 604/22 |
| 2009/0116032 A1 * | 5/2009 | Zara ............................. 356/477 |
| 2009/0221920 A1 * | 9/2009 | Boppart et al. ............... 600/476 |
| 2009/0264768 A1 * | 10/2009 | Courtney et al. ............. 600/463 |
| 2010/0056900 A1 * | 3/2010 | Whitcomb et al. ........... 600/414 |
| 2010/0249601 A1 * | 9/2010 | Courtney ...................... 600/463 |
| 2010/0305452 A1 * | 12/2010 | Black et al. ................... 600/476 |
| 2011/0034832 A1 * | 2/2011 | Cioanta et al. .................... 601/1 |
| 2011/0092781 A1 * | 4/2011 | Gertner ......................... 600/301 |
| 2011/0092880 A1 * | 4/2011 | Gertner ........................... 604/20 |
| 2011/0291321 A1 * | 12/2011 | Chan et al. .................... 264/222 |

OTHER PUBLICATIONS

Suh et al, "Intravascular Detection of the Vulnerable Plaque", Circ Cardiovasc Imaging 2011;4;169-178.*

Sun et al, "Optical coherence elastography: current status and future applications", Journal of Biomedical Optics 16(4), 043001 (Apr. 2011).*

Adie et al, "Spectroscopic optical coherence elastography", Dec. 6, 2010 / vol. 18, No. 25 / Optics Express 25519.*

Grimwood et al, "Elastographic contrast generation in optical coherence tomography from a localized shear stress", Phys. Med. Biol. 55 (2010) 5515-5528.*

Karimi et al, "Estimation of Nonlinear Mechanical Properties of Vascular Tissues via Elastography", Cardiovasc Eng. Dec. 2008; 8(4): 191-202. doi:10.1007/s10558-008-9061-0.*

Xing Liang et al., Optical micro-scale mapping of dynamic biomechanical tissue properties, Optics Express, Jan. 1, 2008, 14 pp., vol. 16, No. 15, Optical Society of America, Washington, DC, US.

Final Rejection for U.S. Appl. No. 13/285,178 dated Aug. 30, 2013.

Office Action dated Apr. 23, 2014 received in corresponding U.S. Appl. No. 13/285,178.

Lu et al., "A noncontact ultrasound indentation system for measurement of tissue material properties using water jet compression". Ultrasound in Med. & Biol., vol. 31, No. 6 2005, pp. 817-826.

Final Office Action received in U.S. Appl. No. 13/285,178 dated Jan. 16, 2015.

* cited by examiner

HIGH SPEED ELASTOGRAPHIC PROPERTY MAPPING OF LUMENS UTILIZING MICROPALPATION DELIVERED FROM AN OCT-EQUIPPED CATHETER TIP

RELATED APPLICATIONS

This application is based on and claims the benefit of U.S. Provisional Patent Application No. 61/475,173, filed Apr. 13, 2011, the entire disclosure of which is incorporated herein by reference.

BACKGROUND OF THE INVENTION

The present invention relates generally to medical imaging, and more specifically to a catheter having a palpator that applies a tip-directed fluid or tip-directed indenter to cause elastographic deformation and an optical coherence tomography (OCT) imager to provide high speed elastographic property mapping.

Vascular catheter based elastography palpation using OCT (OCTe) has been done using global (noninvasive) compression or using the natural blood pressure cycle as the palpation force inducing the observed tissue deformations. Such an approach tends to be slow and incapable of producing high strain gradients, thereby reducing the resolution of the elastographic property mapping and the speed at which the mapping is done. A more recent development provides a combined system that synchronizes OCT and acoustic radiation force for simultaneously imaging and mechanically displacing tissue in a patient as a detection and analytical tool. The combined system provides an endoscopic probe having a piezoelectric element that generates the acoustic force to displace the tissue and an OCT scanner that images the tissue. The mechanical displacement of the tissue can be determined and any cancer and arterial plaques can be recognized from the mechanical displacement. See U.S. Pat. No. 7,999,945.

BRIEF SUMMARY OF THE INVENTION

Embodiments of the present invention provide a catheter having a palpator that applies a directed fluid or mechanical indenter to cause elastographic deformation and an OCT imager to provide high speed elastographic property mapping.

An aspect of the present invention is directed to an optical coherence tomography (OCT) catheter for performing high performance elastographic deformation mapping of tissues and plaques of an interior body. The OCT catheter comprises: a catheter having an elongated catheter body extending longitudinally between a proximal end and a distal end along a longitudinal axis, the catheter body including a distal portion at the distal end and a catheter lumen from the proximal end to the distal end; a palpator, disposed in the distal portion, to apply one of a directed fluid or a mechanical indenter to produce a surface-applied palpation force to a target area of the interior body to mechanically displace the interior body and cause elastographic deformation of the target area of one or more surface and subsurface tissues and plaques; and an OCT imaging sensor, disposed in the distal portion, to direct and deliver an OCT beam for OCT deformation detection including elastographic deformation measurement to provide elastographic mapping of the target area.

The palpator may comprise a thermal microbubble driven emitter to explosively evaporate a fluid to create one or more microbubbles which cause emission of some of the fluid to produce palpating shock waves. The palpator may comprise a flowable liquid jet or orifice to apply a directed fluid flow force for a period. In that case, the palpator is configured to generate pulse pressure in the distal portion to produce pulsed fluid palpation to apply the directed fluid flow force via the flowable liquid jet or orifice.

In some embodiments, the palpation force has a palpation force vector, and the palpation force vector and the OCT beam are substantially concentric. The palpator is configured to apply the directed fluid to produce at least one pair of palpation forces, each pair being in opposite directions. The OCT catheter further comprises a closed balloon disposed around the distal portion and being filled with a liquid that is transparent to OCT wavelengths. The closed balloon is inflatable against a surface of the interior body. Palpation by the palpator and elastographic mapping by the OCT imaging sensor are performed through a balloon wall of the balloon. The OCT catheter further comprises a biasing member to bias the distal portion against the target area of the interior body. The biasing member comprises a balloon which is inflatable to bias the distal portion against the target area of the interior body. The distal portion is in contact with the target area for delivery of the palpation force and has a shape to cause nonuniform tissue deformation and tissue shear strains that are elastographically mappable.

In specific embodiments, the OCT imaging sensor includes a movable reflector to receive light from a light source, and an actuator device to move the movable reflector in at least one of translation or rotation to direct the light to scan across the target area to illuminate the one or more surface and subsurface tissues and plaques before and during delivery of the palpation force. The OCT imaging sensor includes a lens to focus the OCT beam at a distance. The OCT catheter further comprises an acoustic imaging transducer, disposed in the distal portion, to provide ultrasonic imaging of the target area.

In some embodiments, the OCT catheter further comprises a control device to synchronize the palpation force and the OCT beam to perform OCT deformation detection including elastographic deformation measurement to provide elastographic mapping of the one or more surface and subsurface tissues and plaques. The OCT catheter further comprises an analysis module to determine displacement of the target area resulting from delivery of the palpation force. The analysis module is configured to perform OCT deformation detection in a manner which takes into account any simultaneous deformations due to blood flow or perfusion. The analysis module is configured to implement an additional optical analytical modality utilizing at least some common portion of the OCT beam's optical path to produce additional optical spectroscopic information. The analysis module is configured to provide compositional mapping of the target area using both the elastographic deformation measurement and the additional optical spectroscopic information in combination.

In specific embodiments, the OCT catheter further comprises a mechanism to change orientation of the OCT beam and the palpation force to be directed to different target areas of the interior body. The OCT catheter further comprises an analysis module to provide three dimensional mapping of the one or more surface and subsurface tissues and plaques of the interior body based on OCT deformation detection including elastographic deformation measurement by the OCT imaging sensor of the different target areas of the interior body. Deformations detected in the OCT deformation detection include both temporary deformations and permanent plastic deformations, the temporary deformations being at least one of elastic or viscoelastic.

Another aspect of the invention is directed to a method for performing elastographic deformation mapping of tissues and plaques. The method comprises: introducing a distal portion of a catheter to an interior of an interior body of a patient, the catheter including an elongated catheter body extending longitudinally between a proximal end and a distal end along a longitudinal axis, the catheter body including the distal portion at the distal end and a catheter lumen from the proximal end to the distal end; applying, from a palpator in the distal portion, one of a directed fluid or a mechanical indenter to produce a surface-applied palpation force to a target area of the interior body to mechanically displace the interior body and cause elastographic deformation of the target area of one or more surface and subsurface tissues and plaques; and directing and delivering an OCT (optical coherence tomography) beam, from an OCT imaging sensor in the distal portion, for OCT deformation detection including elastographic deformation measurement to provide elastographic mapping of the target area.

These and other features and advantages of the present invention will become apparent to those of ordinary skill in the art in view of the following detailed description of the specific embodiments.

DETAILED DESCRIPTION OF THE INVENTION

Figure 1:
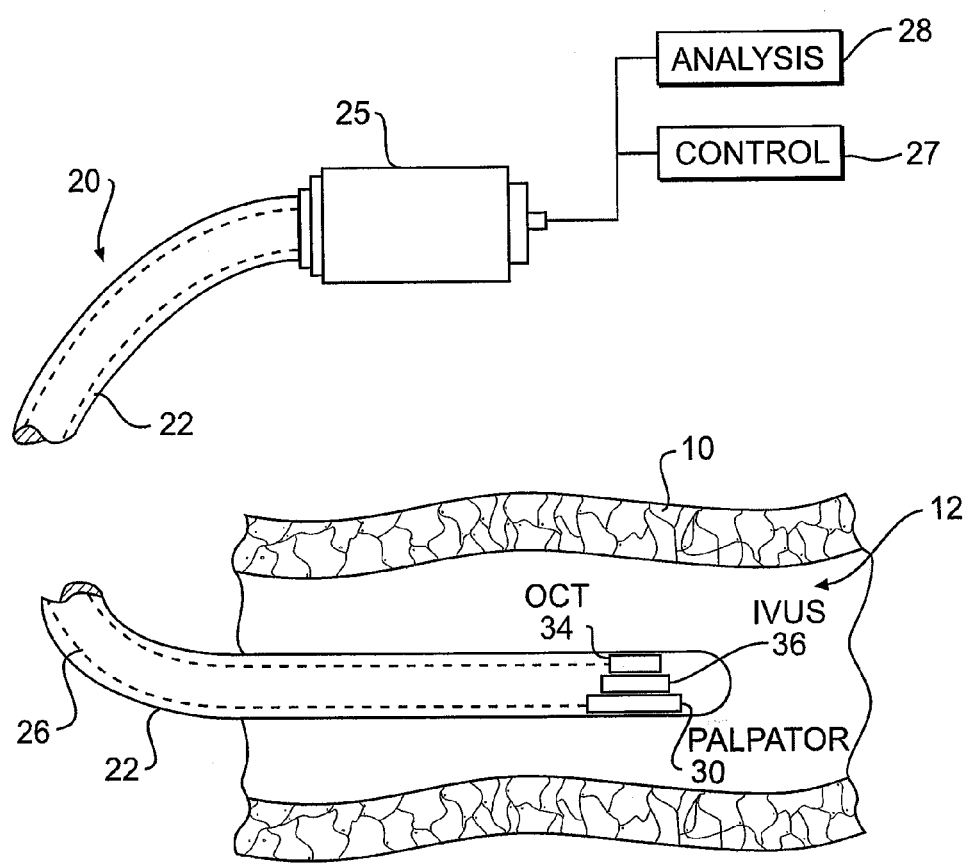
FIG. 1 shows a catheter device disposed in a vessel of a patient to provide high speed elastographic property mapping of the lumen utilizing micropalpation delivered from an OCT-equipped catheter tip portion.

In the following detailed description of the invention, reference is made to the accompanying drawings which form a part of the disclosure, and in which are shown by way of illustration, and not of limitation, exemplary embodiments by which the invention may be practiced. In the drawings, like numerals describe substantially similar components throughout the several views. Further, it should be noted that while the detailed description provides various exemplary embodiments, as described below and as illustrated in the drawings, the present invention is not limited to the embodiments described and illustrated herein, but can extend to other embodiments, as would be known or as would become known to those skilled in the art. Reference in the specification to "one embodiment," "this embodiment," or "these embodiments" means that a particular feature, structure, or characteristic described in connection with the embodiment is included in at least one embodiment of the invention, and the appearances of these phrases in various places in the specification are not necessarily all referring to the same embodiment. Additionally, in the following detailed description, numerous specific details are set forth in order to provide a thorough understanding of the present invention. However, it will be apparent to one of ordinary skill in the art that these specific details may not all be needed to practice the present invention. In other circumstances, well-known structures, materials, circuits, processes and interfaces have not been described in detail, and/or may be illustrated in block diagram form, so as to not unnecessarily obscure the present invention.

In the following description, relative orientation and placement terminology, such as the terms horizontal, vertical, left, right, top and bottom, is used. It will be appreciated that these terms refer to relative directions and placement in a two dimensional layout with respect to a given orientation of the layout. For a different orientation of the layout, different relative orientation and placement terms may be used to describe the same objects or operations.

Exemplary embodiments of the invention, as will be described in greater detail below, provide a catheter having a palpator that applies a directed fluid or, alternatively, a mechanical indenter, to cause elastographic deformation and an OCT imager to provide high speed elastographic property mapping.

FIG. 1 shows a catheter device disposed in a vessel of a patient to provide high speed elastographic property mapping of the lumen utilizing one of fluidically pressurized or indenter-based micropalpation delivered from an OCT-equipped catheter tip portion. The catheter (shown), scope or endoscopic supporting device may be introduced into a patient via a lumen, natural orifice, or manmade surgical puncture to perform one or both of a diagnostic function and a therapeutic function on an organ or tissue such as, for example, brain heart, liver, kidney, pancreas, spleen, and neural/CNS tissue. As seen in FIG. 1, the vessel 10 has a vessel wall that defines a lumen 12 such as a blood lumen. The vessel 10 is merely illustrative; the catheter device may be placed in some other cavity for mapping a different anatomy of the patient. The catheter 20 has an elongated catheter body 22 extending longitudinally between a proximal end and a distal end along a longitudinal axis. The catheter body 22 includes a distal portion or distal tip 24 at the distal end, a catheter lumen 26 from the proximal end to the distal end, and typically a handle 25 at the proximal end to manipulate or operate the catheter body 22 and/or other components such as a palpator, OCT components, sensors, and the like in the tip 24. The catheter 20 may be introduced into the lumen 12 of the vessel 10 using a guidance sheath or guiding wire (neither shown), or the like.

The catheter 20 is an OCT catheter for performing high resolution elastographic deformation mapping of tissues and plaques. The catheter 20 includes a palpator 30, disposed in the distal portion 24, to apply one of a directed fluid or a movable indenter to produce a surface-applied palpation force to a target area of an interior body such as the vessel wall to mechanically displace the interior body and cause elastographic deformation of the palpated target area of one or more surface and subsurface tissues and plaques. By "surface applied" we mean that the palpating force is directed only upon the tissue surface and that all deformations in the surface and subsurface tissue have their origin in the surface force and any inward pushing of the tissue from that surface. Clearly prior art acoustic radiation force applied at depth directly is not included in this definition. An OCT imaging sensor 34 is disposed in the distal portion 24 to direct and deliver an OCT beam for OCT deformation detection including elastographic deformation measurement to provide elastographic mapping of the target area. The deformations detected in the OCT deformation detection include both temporary elastic and/or viscoelastic deformations and possibly some permanent plastic deformations. An optional acoustic imaging sensor 36 (not used as a radiation-force palpator) is also disposed in the distal portion 24 to provide ultrasonic imaging of the target area. Thus, the device depicted in FIG. 1 is a combined OCT/IVUS catheter with OCT-based elastographic analysis capabilities. A control device 27 is provided to control operation of the components in the distal portion 24 to obtain the data for elastographic deformation mapping, as described below. An analysis module 28 is provided to analyze the data, as described below.

Figure 2A:
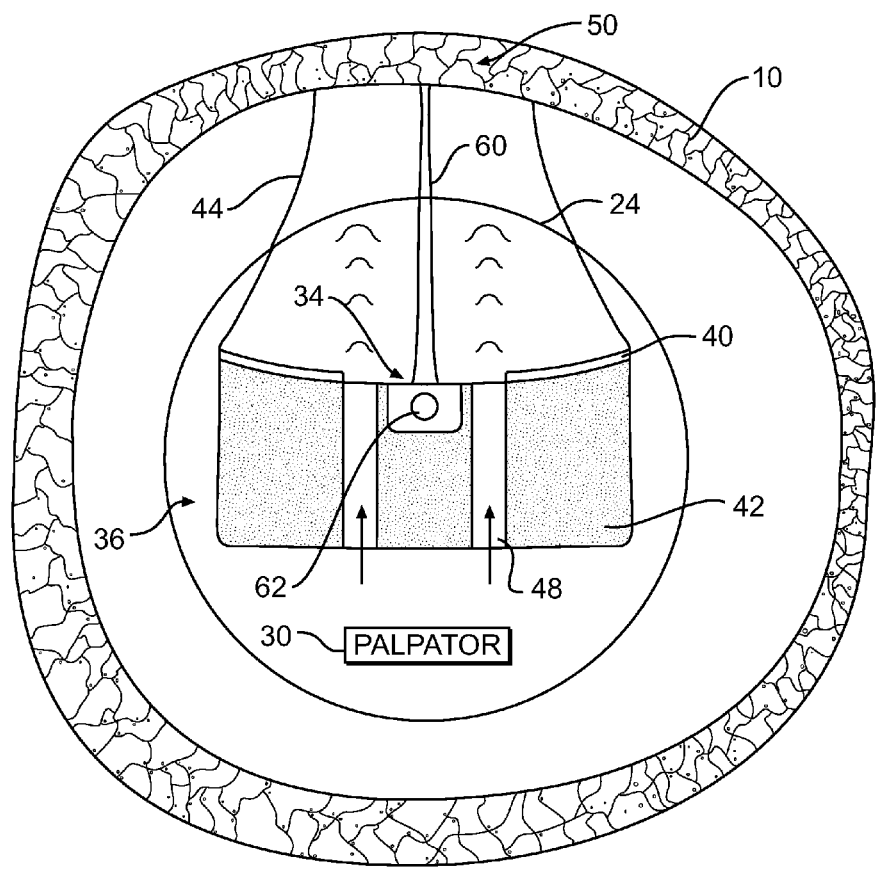
FIG. 2A is a partial sectional view of the distal portion of the catheter showing the fluidic palpator, OCT imaging sensor, and acoustic imaging sensor according to an embodiment of the invention.

FIG. 2A is a partial sectional view of the distal portion 24 of the catheter 20 showing the fluidic palpator 30, OCT imaging sensor 34, and acoustic imaging sensor 36 according to an embodiment of the invention. The distal portion 24 is typically surrounded by blood, saline, contrast agent, or a mixture thereof. The acoustic imaging sensor 36 includes an acoustic transducer 40 (typically piezoceramic) and attenuative backer 42. FIG. 2A shows an outline 44 of the acoustic beam 44 from the acoustic imaging sensor 36. This optional sensor 36 acts as an intravascular ultrasound (IVUS) imaging transducer to provide measurements of lumen and vessel size, plaque area and volume, and the location of key anatomical landmarks. The ultrasound imaging can be combined with ultrasonic spectral analysis of echoes for composition and structure. For example, Volcano's VH® IVUS technology is marketed as helping to differentiate the four plaque types: fibrous, fibro-fatty, necrotic core and dense calcium. IVUS provides relatively far field imaging (e.g., extending to several mm) while OCT provides relatively nearer field imaging (e.g., performing best within about 2 mm) but at 10X finer resolution.

The palpator 30 of FIG. 2A applies a directed fluid to produce a fluidic palpation force or shockwaves. Relative to prior art radiation-force palpation, the inventive fluidic palpation (or indenter palpation discussed below) can apply higher forces or can apply deforming forces over a broader area from a tissue (internal or external) surface without the complexity of a focused or scanned palpation transducer. Although acoustic palpation can focus palpation at depth inside tissue, the fact is that for our lumen based applications herein, the tissues of interest are relatively shallow comprising much of the near-field lumen walls, i.e. at depth focusing is not necessary. Our fluidic (or indenter-based) palpation can provide detectable strains over a much broader region directly in front of the tip 24, while at the same time limiting the maximum strain so as to avoid rupturing fragile plaques or fibrous caps. Our fluidic and indenter palpators can also palpate without any appreciable heating of the tissue target or of the tip 24 unlike radiation-force palpation. They are ideally designed for near field tissue elastographic property mapping by applying a gently varying (therefore still locally deforming in the area of interest) nonuniform load over a wide area in front of the tip 24.

In FIG. 2A, the directed fluid or fluid shockwaves will flow through one or more openings or channels 48 in the backer 42 of the acoustic imaging sensor 36 to produce fluidic palpation waves toward a target area 50 of tissues and/or plaques. The acoustic imaging transducer 40 of the optional acoustic imaging sensor 36 and the OCT sensor 34 are also directed to the target area 50. The directed palpating fluid or fluid shockwaves may take the form of a pulsed saline jet that is energized within the distal portion 24 of the catheter 20. One way to generate the directed fluid is by providing in the distal portion 24 a thermal microbubble driven emitter as the palpator 30 to explosively evaporate a fluid to create one or more microbubbles which cause emission of some of the fluid to produce palpating shockwaves. By "explosive evaporation' is meant, in the known sense, that bubble growth rates are fast enough to produce shock waves and pronounced pressure spikes. This flash evaporation approach is akin to inkjet printing that utilizes a thermal ink jet or steam bubbles in the fluid to drive the fluid toward the target. Hewlett-Packard and Canon have shipped tens of millions of inkjet printers using such proven phenomenon. Another way to generate the directed fluid is by providing a flowable liquid jet or orifice to apply a directed fluid flow force for a sustained period such as for milliseconds, tens of milliseconds or tenths of a second. In one preferred embodiment, the palpator 30 is configured to generate pulse pressure in the distal portion 24 to produce pulsed fluid palpation to apply the directed fluid flow force via the flowable liquid jet or orifice. For example, a positive displacement transducer such as a PZT diaphragm or piezo-membrane can be electrically actuated to bend in shear mode and generate the pulse pressure to produce the pulsed fluid palpation. Note that this is not MHz-range acoustic radiation force palpation wherein focused acoustics deform subsurface tissue; rather, it is very low frequency (KHz range, unusable for IVUS imaging) fluidic deformation of tissue which acts from only the tissue surface. Providing the palpator 30 in the distal portion 24 avoids losing low frequency (KHz range) palpation content as would be the case if pressure excitation were remotely applied from the proximal end of the catheter 20 and the higher frequency components were damped out. Such low frequency shockwaves or fluid pulses can be created using nonfocused bending piezo-actuators or piezo-membranes or the microbubbles mentioned above.

Figure 2B:
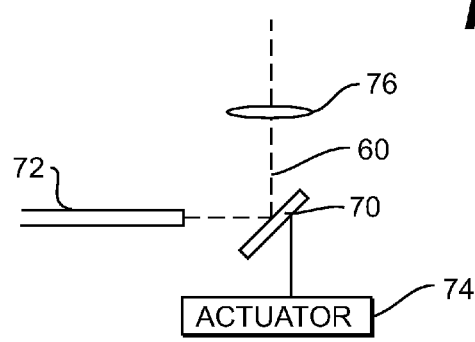
FIG. 2B schematically illustrates an example of the OCT imaging sensor.

The OCT sensor 34 in FIG. 2A produces an OCT beam 60 directed toward the target area 50. Preferably, the palpation force vector of the palpation generated by the palpator 30 and the OCT beam 60 of the OCT imaging sensor 34 (as well as the acoustic beam 44 of the optional acoustic imaging sensor 36) are substantially concentric or coaxial (e.g., within a few degrees angularly and/or within a small distance that is no more than a few percentages of the diameter of the distal portion 24 and preferably are perfectly concentric. FIG. 2A shows that the OCT optical imaging fiber or optical energy delivery conduit 62 is preferably centrally located within the acoustic emitter of the acoustic imaging sensor 36 and centrally located with respect to the directed flowed fluid or fluid shockwaves. Any suitable configuration of the OCT imaging sensor 34 may be employed. In one example as seen in FIG. 2B, the OCT imaging sensor 34 includes a movable reflector/mirror 70 to receive light, typically via an optical fiber 72, from a light source (typically outside the catheter 20 and supplied near or through the proximal end of the catheter 20), and an actuator device 74 to move the movable reflector 70 in at least one of translation or rotation to direct the light to scan across the target area 50 to illuminate one or more of the tissues and plaques before and during delivery of the palpation force by the palpator 30. An optical lens 76 may be used to focus the OCT beam 60 at a distance. In FIG. 2B the palpator (not shown) could be concentric around the OCT beam as shown in earlier FIG. 2A. Rotation of the catheter tip 24 may instead or in addition provide spatial scanning of the OCT and palpator.

The components in the distal portion 24 can perform any or all of OCT imaging, IVUS imaging, and elastographic OCT-based or elastographic IVUS-based mapping. Recall that OCT-based elastography has superior sensitivity and resolution relative to IVUS based elastography; however, OCT elastography is restricted to the first couple of millimeters or so. The near field OCT-based (or even far field IVUS-based) elastographic mapping may use the palpation of the palpator 30 and OCT based deformation detection of the OCT sensor 34 for high resolution in the near field (e.g., within about 2 mm), and may use palpation of the palpator 30 and ultrasound based deformation detection of the acoustic imaging sensor 36 for lower resolution elastography in the far field (e.g., beyond about 2 mm).

Any elastographic mapping technique will map deformations determined by examining or comparing images before and after a mechanical palpation load is applied (or more correctly at two different load states). The technique is called elastography implying fully reversible elastic recovery upon load removal but herein by "elastography" we mean more broadly the mapping of palpation-induced deformations regardless of their recovery times or even if they ever recover. We again stress that for elastography, it is desirable to apply a palpation force having a finite force gradient (i.e., an uneven force) such that all loaded tissues are at least somewhat deformed, at least in shear). Uniaxial deformations, if any, are also detected; however, these tend to be small given tissue incompressibility. Even incompressible materials undergo shear. The distal portion 24 preferably has a shape such that when it is biased against the vessel wall target area 50, it will provide nonuniform tissue deformation and hence tissue shear strains that are elastographically mappable. As an example, the tip 24 contact surface to tissue could be slightly domed such that there is more deformation in the center than at the edges when the tip 24 is pressed into the tissue. If this provides sufficient deformation, one might even avoid the fluidic and indenter options also described herein, as the tip is itself a shaped indenter.

A known way to present elastographic data is simply to apply a color scale map such as one in which large deformations are magenta, somewhat lesser deformations red, and somewhat lesser deformations orange, and even lesser deformations green. Thus, green areas are harder and stiffer. This provides a color-coded version of the image in the modality used to measure deformations (e.g., OCT or ultrasound). Such a scale might be linear or logarithmic. The inventive devices taught herein present new possibilities for tissue analysis wherein one uses information from two or more modalities to deduce composition or structure. For example, for a device having OCT imaging plus IVUS imaging plus acoustic or indenter palpation, tissue composition/structure is deduced from a combination of (OCT and/or IVUS images) plus elastography utilizing OCT deformation mapping made possible by fluidic or indenter-based inventive palpation. Elastography imaging while pulling a spinning or angulating OCT and palpator along a vessel lumen can produce a 3D elastographic image or a 3D compositional or structure image. The same consistent color coding can preferably be used in different modalities. Those skilled in acoustics and elastography know that there are several methods, such as described in U.S. Pat. No. 7,999,945, to detect and compute tissue deformations and we include all such known and future methods in the scope herein.

The control device 27 controls operation of the palpator 30 and the OCT imaging sensor 34, and the optional acoustic imaging sensor 36 as well if it is provided. More specifically, the control device 27 preferably synchronizes the application of palpation force and the OCT beam to perform OCT deformation detection including elastographic deformation measurement to provide elastographic mapping of the tissue/plaques. If the optional acoustic imaging sensor 36 is provided, its sensing operation (as IVUS) can also be synchronized with the palpation force as well.

The analysis module 28 is provided to determine a displacement map or image of the target area 50 resulting from delivery of the palpation force. Using a variety of mathematical and image-analysis techniques cited above, one obtains a 2D sectional map of vessel wall elasticity. One may also obtain a 3D deformation map such as based on multiple parallel 2D maps. Known OCT and IVUS pullback methods would allow for inventive 3D compositional maps. Vessel wall elasticity is known to vary over more than four orders of magnitude depending on vascular or plaque compositions and mixtures. Such a range of variation typically requires a logarithmic color scale. In one preferred embodiment, OCT motion tracking (deformation tracking) is done in the phase mode as opposed to the historically older speckle mode since such tracking is easier in the phase mode. The combined OCT/IVUS imaging provided at the distal portion 24 of the catheter 20 can provide pseudo real-time gray-level or B-Mode maps of OCT B-mode tissue contrast, IVUS B-Mode tissue contrast, and elastic maps of at least near tissues with presumed compositions and/or structures. By preferably also doing some simultaneous infrared compositional spectroscopic analysis, one can obtain all the information needed to determine follow-up therapies in a manner wherein composition is determined by both elasticity and spectroscopy, but at least by elasticity. Moreover, OCT deformation detection may utilize optical phase or phase-Doppler information. Such OCT optical phase information may also provide information on vessel lumen or other fluid flow or flowability as in optical Doppler flow sensing. Mapped tissue properties may start with assumed values before their computationally iterated finalization.

In specific embodiments, the analysis module 28 is configured to perform OCT deformation detection in a manner which takes into account any simultaneous deformations due to blood flow or perfusion (e.g., to determine displacement of the target area resulting from blood flow and heartbeat of the patient without the palpation force, and to subtract out or otherwise compensate for the displacement taking place without the palpation force from the displacement obtained with the palpation force). The analysis module 28 may be configured to implement an additional optical analytical modality such as Raman compositional spectroscopy utilizing at least some common portion of the OCT beam's optical path to produce additional optical spectroscopic information. The analysis module 28 may be configured to provide compositional mapping of the target area using both the elastographic deformation measurement and the additional optical spectroscopic information in a combined or weighted algorithm. Such compositional maps could be overlaid in color on the gray-level OCT, IVUS or OCT/IVUS combo image.

The catheter 20 includes a mechanism to change the orientation of the OCT beam 60 and the palpation force to be directed to different target areas of the vessel wall. For example, the mechanism can rotate the palpator 30 and the OCT imaging sensor 34 around in the circumferential direction and move them in axial translation. This can be done by moving the entire distal portion 24 in rotation and translation. The mechanism can be provided near the handle 25 or as part of the handle 25 that controls movement of the catheter body 22 and the distal portion 24. As such, the analysis module 28 can provide three dimensional mapping of tissues and plaques of the vessel wall based on OCT deformation detection including elastographic deformation measurement by the OCT imaging sensor 34 of the different target areas of the vessel wall.

It may be desirable to avoid (or account for) reactive catheter tip drift which may result from sustained palpation forces. The reason is that if the tip 24 reactively moves opposite to the applied palpation force during sustained palpation force application, then the applied sustained palpation force may be less than assumed in the elastographic calculations.

For short palpation pulses, the lateral inertia and drag of the tip 24 (along the axis transverse to the lumen and collinear with the palpation force) can appreciably avoid such drift. If one only desires a normalized elastographic map which primarily depicts hardness gradients, then this is not an issue either. However, if absolute hardness or rigidity is to be mapped, then one needs to avoid or account for reactive tip motions during palpation force application. One way to cancel or reduce catheter tip drift is to configure the palpator 30 to apply the directed flowed fluid or fluid shockwaves to produce at least one pair of palpation forces, each pair being in opposite cancelling directions.

Figure 3:
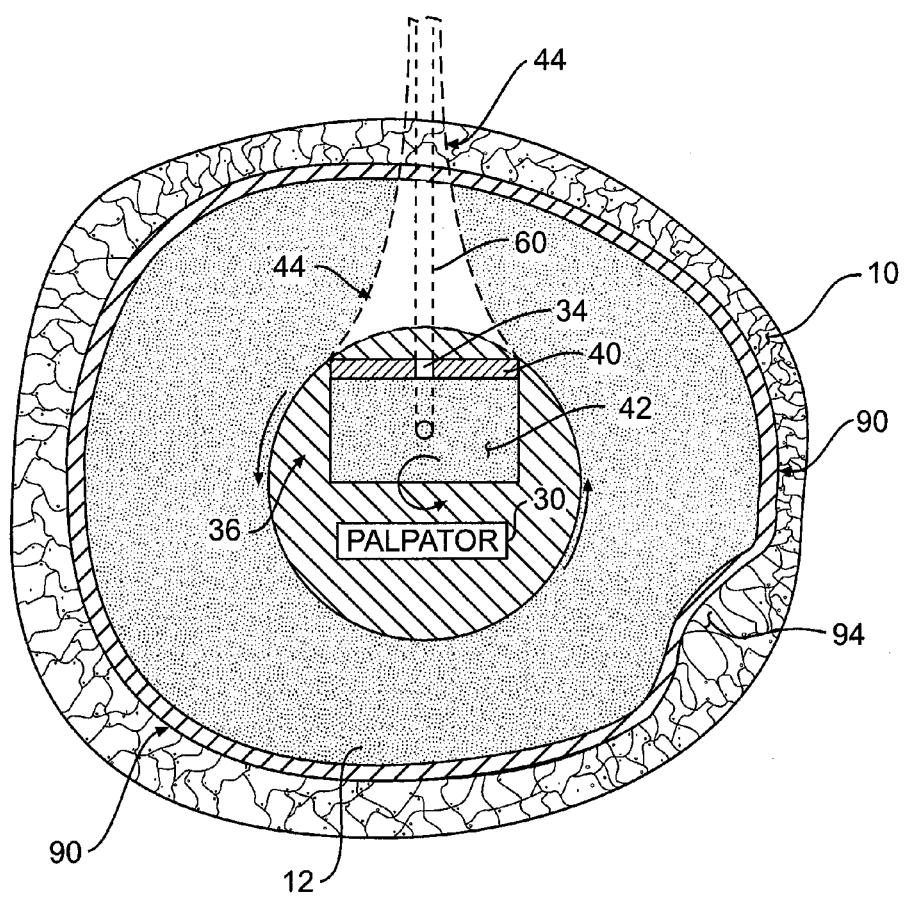
FIG. 3 is a partial sectional view of the distal portion of the catheter showing a balloon around the distal portion according to another embodiment of the invention.

Additionally or alternatively, the palpation forces may be applied through or past a balloon, a standoff, or a membrane material. FIG. 3 is a partial sectional view of the distal portion 24 of the catheter 20 showing a balloon 90 around the distal portion 24 according to another embodiment of the invention. The closed balloon 90 is preferably filled with a liquid that is transparent to OCT beam wavelengths, such as saline. The closed balloon 90 is a part of the catheter 20 in the form of a balloon-containing catheter tip and is inflatable with the liquid against surfaces of the tissues and plaques of the vessel 10. The vessel 10 has a blood lumen 12 of generally circular cross section. The depicted vessel wall is of generally uniform thickness except for an area 94 where deposits thereon or therein cause a bulge inwards. The inflated balloon 90 helps to position the distal portion 24 containing the palpator 30 and sensors 34, 36 generally centrally in the vessel lumen 12 in a manner commonly known for therapeutic balloon-containing catheter tips. The balloon 90 is made of a flexible and compliant material so as to inflate conformally over the lump area 94 and would also act to stabilize any fragile vessel wall tissues or plaques and prevent their rupture during scanning with the inventive device.

In operation, the balloon 90 is inflated after the distal portion 24 is disposed at a desired axial location along the vessel lumen 12 and the inflated balloon 90 then serves to centrally locate and mechanically clamp or fix the distal portion 24 of the catheter 20 at the approximate center of the vessel lumen 12. The balloon 90 may be partially inflated to act as an atraumatic bumper to prevent scraping of the lumen wall and then, when in place, fully inflated to clamp the tip 24 in place and perform tissue evaluation. Off-center positioning (not shown in FIG. 3) is also within the scope. In this way, the vessel wall, all 360 degrees around the distal portion 24, is within reach of the OCT beam 60. Furthermore, when the palpator 30 generates a fluidic palpation force or shock from the distal portion 24 in one direction toward the target area 50, the reactive force in the opposite direction will not drive the distal portion 24 in that opposite direction away from the target area 50 as the balloon helps maintain the shown central location. The balloon 90 offers a significant safety improvement, especially if the vessel wall contains a known and dangerous rupturable membrane with underlying fluid. The closed balloon 90 further prevents blood in the vessel lumen 12 from mixing with the saline inside the balloon 90. Saline advantageously is highly transparent to OCT beam wavelengths. It is noted that one might even use the inflated balloon 90 to fluidically "palpate" the vessel wall with sustained fluidic forces or with short fluidic shockwaves. A shaped balloon or a balloon with a fluid jet inside of it can both apply a nonuniform palpation force and produce mappable deformations. The balloon 90 could alternatively have a hole through or around it (not shown in FIG. 3, shown in FIG. 4A) to allow some blood flow during tissue assessment.

The elastography results from the catheter devices of this invention can provide guidance, feedback, or advice with regard to the delivery of one or more therapies, surgeries, or implantable devices (e.g., manmade or tissue-based stents or grafts) into, to, from, or through a vessel lumen, as well as the installation, maintenance, or removal of such implantable devices. The elastography results can also provide guidance, feedback, or advice with regard to the safety or potential beneficial treatment of a fibrous cap in a vessel lumen. The elastography results can further provide guidance, feedback, or advice with regard to the delivery of a drug that is being considered for delivery, or a drug that is already being delivered, or a drug for which current delivery may be discontinued or modulated in dosage.

The acoustic transducer 40, if employed, can also be used to drive a drug into a tissue for acoustically aided or enhanced drug delivery, erode or remove undesired lumen deposits or growths (e.g., by cavitating the lumen blood to emulsify the deposits or growths), and/or perform one or more of acoustic athermal, cavitational, or thermal therapy on vessel lumen tissue.

Figure 4A:
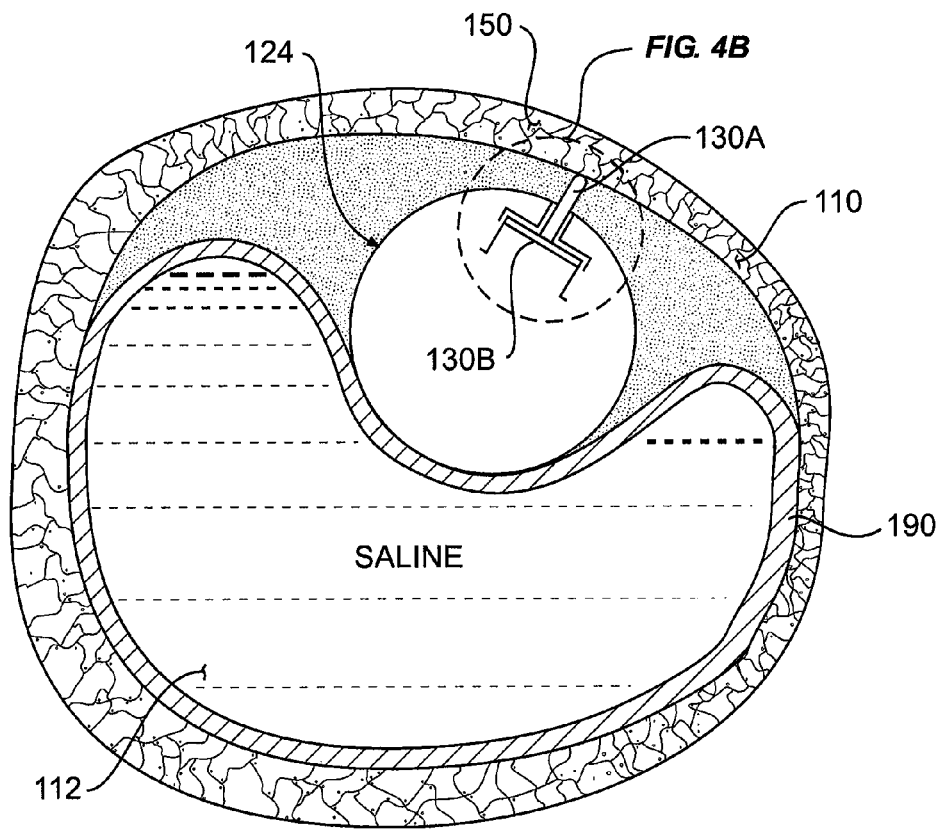
FIG. 4A is a partial sectional view of the distal portion of the catheter showing the palpator utilizing a mechanical indenter according to another embodiment of the invention.
Figure 4B:
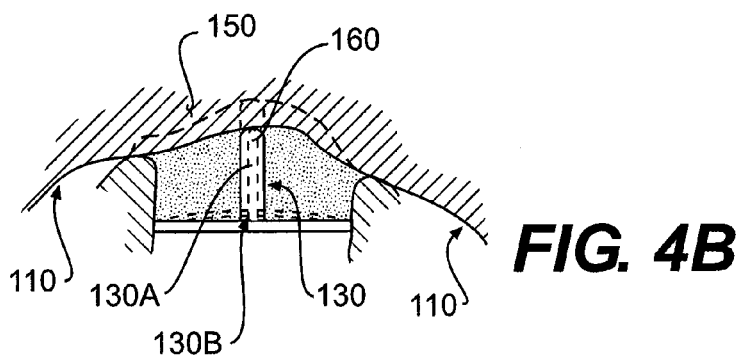
FIG. 4B is an enlarged view of the mechanical indenter of FIG. 4A.

FIG. 4A is a partial sectional view of the distal portion of the catheter showing the palpator utilizing a mechanical indenter according to another embodiment of the invention. The OCT imaging sensor and the optional acoustic imaging sensor are omitted for simplicity. The mechanical indentation member is used to deform tissue rather than the directed fluid flow or fluid shockwaves of FIG. 2A. In FIG. 4A, the distal portion or tip 124 includes the mechanical indenter palpator 130 (130A, 130B). The indenter 130 is shown biased against an interior lumen wall of the vessel 110 by an inflatable balloon 190 such that a tissue region 150 can be mapped. The balloon 190 may be inflated with saline 112 or the like. In the breakout or expanded view of FIG. 4B, it can be seen that the particular indenter example has a pin type indenter 130A which is axially pressed into the target area tissue 150 as by deflection of its supporting membrane 130B. The membrane 130B could easily be, for example, a saline pressure activated membrane. FIG. 4B depicts the OCT port or beam 160 emanating from the indenter pin 130A but it may be situated anywhere facing the target area tissue 150 where it has the desired field of view.

Of key importance in any mechanical-pusher type palpation (such as the palpator pin 130A) is that the palpation force goes substantially into usefully deforming the target area tissue 150 and not uselessly translating the entire catheter tip 124 backwards. There are a few ways to accomplish this.

First, as depicted in FIG. 4A, one could bias the tip 124 against the target area tissue 150 using a biasing balloon 190. Alternatively, in a manner somewhat similar to the balloon 190 of FIG. 4A, one could place the biasing balloon instead between the tip 124 and the target area tissue 150 (not shown) and observe through the balloon. As seen in FIG. 4A, the tip 124 is lightly pressed against the target area tissue 150 using the pressurized balloon 190 and the palpator pin 130A can be activated to locally palpate the target area tissue 150 in front of the tip 124 as depicted in the breakout. The balloon 190 may or may not be an integral part of the catheter supporting tip 124. Further, the biasing balloon 190 may have an inflation pressure which is varied between a higher value and a lower value, the lower value allowing for sliding of the tip 124 axially to scan a new target area tissue portion 150 and the higher value being used to fixedly hold the tip 124 at a particular axial position for palpating scanning. It is noted that with a biasing balloon 190 and a tip 124 which has a curved tissue contacting surface, that the tip curved surface could be forced into the target area tissue 150 while performing OCT thereby making the curved tip itself the indenting palpator. Along similar lines, the embodiment of FIG. 4A could use, instead of a balloon 190, a backward-directed fluid jet or an internal tip-bending mechanism (neither shown) to force the tip 124 into the target area tissue 150.

A second useful tool would be the provision of a suction clamping feature (not shown) on the probe tip 124. Such suction clamping, applied over the entire contacting face of the probe tip 124 and juxtaposed target area tissue 150, would pull the tip 124 against the tissue 150 and serve as another form of biasing the tip 124 against the vessel wall target region 150. Using that approach, one could either observe deformations as the tissue is deformed by a settling curved-face tip or complete the suction clamping and then have a dedicated mechanical palpator such as palpator 130 perform palpation. This clamping approach could even be utilized from within a balloon such as that of FIG. 3 thereby precluding the generation of debris from the lumen wall. For small lumens with potential plaque debris being generated, we prefer the balloon clamping of FIGS. 3 and 4 over the suction approach.

In the description, numerous details are set forth for purposes of explanation in order to provide a thorough understanding of the present invention. However, it will be apparent to one skilled in the art that not all of these specific details are required in order to practice the present invention. Additionally, while specific embodiments have been illustrated and described in this specification, those of ordinary skill in the art appreciate that any arrangement that is calculated to achieve the same purpose may be substituted for the specific embodiments disclosed. For example, the tip electrode may also serve as a sensing or pacing electrode or may include a tissue or trench sensor or imaging device. This disclosure is intended to cover any and all adaptations or variations of the present invention, and it is to be understood that the terms used in the following claims should not be construed to limit the invention to the specific embodiments disclosed in the specification. Rather, the scope of the invention is to be determined entirely by the following claims, which are to be construed in accordance with the established doctrines of claim interpretation, along with the full range of equivalents to which such claims are entitled.

What is claimed is:

1. A method for performing elastographic deformation mapping of tissues and plaques, the method comprising:
    introducing a distal portion of a catheter to an interior of an interior body of a patient, the catheter including an elongated catheter body extending longitudinally between a proximal end and a distal end along a longitudinal axis, the catheter body including the distal portion at the distal end and a catheter lumen from the proximal end to the distal end, the distal portion including a supporting member;
    applying, from a palpator in the distal portion, a mechanical indenter pin, to move the mechanical indenter pin axially along a longitudinal axis of the mechanical indenter pin relative to the distal portion, to contact the target area of the interior body, to produce a surface-applied palpation force to the target area of the interior body to mechanically displace the interior body and cause elastographic deformation of the target area of one or more surface or subsurface tissues or plaques; and
    directing and delivering an OCT (optical coherence tomography) beam, from an OCT imaging sensor in the distal portion, for OCT deformation detection including elastographic deformation measurement to provide elastographic mapping of the target area;
    wherein the mechanical indenter pin is moved axially along the longitudinal axis of the mechanical indenter pin, relative to the distal portion, by the supporting member in the distal portion.

2. The method of claim 1,
    wherein the OCT beam emanates from an opening along the longitudinal axis of the mechanical indenter pin.

3. The method of claim 1,
    wherein the palpation force has a palpation force vector, and the palpation force vector and the OCT beam are substantially concentric.

4. The method of claim 1, further comprising:
    providing a closed balloon around the distal portion, filling the closed balloon with a liquid that is transparent to OCT wavelengths, and inflating the closed balloon against a surface of the interior body.

5. The method of claim 4,
    wherein the applying and the directing and delivering are performed through a balloon wall of the balloon.

6. The method of claim 1, further comprising:
    inflating a balloon to bias the mechanical indenter pin against the target area of the interior body.

7. The method of claim 1, further comprising:
    performing, from an acoustic imaging transducer in the distal portion, ultrasonic imaging of the target area.

8. The method of claim 1, further comprising:
    synchronizing the palpation force and the OCT beam to perform OCT deformation detection including elastographic deformation measurement to provide elastographic mapping of the one or more surface or subsurface tissues or plaques.

9. The method of claim 1, further comprising:
    determining displacement of the target area resulting from delivery of the palpation force.

10. The method of claim 1, further comprising:
    performing OCT deformation detection in a manner which takes into account any simultaneous deformations due to blood flow or perfusion.

11. The method of claim 1, wherein directing and delivering the OCT beam for OCT deformation detection produces optical spectroscopic information including elastographic deformation measurement, the method further comprising:
    implementing an additional optical analytical modality utilizing at least some common portion of the OCT beam's optical path to produce additional optical spectroscopic information.

12. The method of claim 11, further comprising:
    providing compositional mapping of the target area using both the elastographic deformation measurement and the additional optical spectroscopic information in combination.

13. The method of claim 1, further comprising:
    changing orientation of the OCT beam and the palpation force to be directed to different target areas of the interior body.

14. The method of claim 13, further comprising:
    providing three dimensional mapping of the one or more surface or subsurface tissues or plaques of the interior body based on OCT deformation detection including elastographic deformation measurement by the OCT imaging sensor of the different target areas of the interior body.

15. The method of claim 1,
    wherein deformations detected in the OCT deformation detection include both temporary deformations and permanent plastic deformations, the temporary deformations being at least one of elastic or viscoelastic.

16. A method for performing elastographic deformation mapping of tissues and plaques, the method comprising:
- introducing a catheter to an interior of an interior body of a patient, the catheter including an elongated catheter body extending longitudinally between a proximal end and a distal end along a longitudinal axis;
- applying, from the catheter, a mechanical indenter pin, to move the mechanical indenter pin axially along a longitudinal axis of the mechanical indenter pin relative to the catheter body, to contact the target area of the interior body, to produce a surface-applied palpation force to the target area of the interior body to mechanically displace the interior body and cause elastographic deformation of the target area of one or more surface or subsurface tissues or plaques; and
- directing and delivering an OCT (optical coherence tomography) beam, from the catheter, for OCT deformation detection including elastographic deformation measurement to provide elastographic mapping of the target area;
- wherein the mechanical indenter pin is moved axially along the longitudinal axis of the mechanical indenter pin, relative to the catheter body, by a pressure activated membrane in the catheter body.

17. The method of claim 16,
wherein the OCT beam emanates from an opening along the longitudinal axis of the mechanical indenter pin.

18. An optical coherence tomography (OCT) catheter for performing elastographic deformation mapping of tissues and plaques of an interior body, the OCT catheter comprising:
- a catheter having an elongated catheter body extending longitudinally between a proximal end and a distal end along a longitudinal axis, the catheter body including a distal portion at the distal end and a catheter lumen from the proximal end to the distal end, the distal portion including a supporting member;
- a mechanical indenter pin disposed in the distal portion, the mechanical indenter pin being movable axially along a longitudinal axis of the mechanical indenter pin relative to the distal portion, by the supporting member in the distal portion, to contact a target area of the interior body, to produce a surface-applied palpation force to the target area of the interior body to mechanically displace the interior body and cause elastographic deformation of the target area of one or more surface or subsurface tissues or plaques; and
- an OCT imaging sensor, disposed in the distal portion, to direct and deliver an OCT beam for OCT deformation detection including elastographic deformation measurement to provide elastographic mapping of the target area.

19. The OCT catheter of claim 18, further comprising:
- a closed balloon disposed around the distal portion and being filled with a liquid that is transparent to OCT wavelengths;
- wherein the closed balloon is inflatable against a surface of the interior body.

20. The OCT catheter of claim 18, further comprising:
- a balloon which is inflatable to bias the mechanical indenter pin against the target area of the interior body.

21. The OCT catheter of claim 18,
wherein the mechanical indenter pin includes an opening along the longitudinal axis of the mechanical indenter pin through which the OCT imaging sensor directs the OCT beam.

22. An optical coherence tomography (OCT) catheter for performing elastographic deformation mapping of tissues and plaques of an interior body, the OCT catheter comprising:
- a catheter having an elongated catheter body extending longitudinally between a proximal end and a distal end along a longitudinal axis, the catheter body including a distal portion at the distal end and a catheter lumen from the proximal end to the distal end;
- a mechanical indenter pin disposed in the distal portion, the mechanical indenter pin being movable axially along a longitudinal axis of the mechanical indenter pin relative to the catheter body, by a pressure activated membrane in the catheter body, to contact a target area of the interior body, to produce a surface-applied palpation force to the target area of the interior body to mechanically displace the interior body and cause elastographic deformation of the target area of one or more surface or subsurface tissues or plaques; and
- an OCT imaging sensor, disposed in the distal portion, to direct and deliver an OCT beam for OCT deformation detection including elastographic deformation measurement to provide elastographic mapping of the target area.

23. The OCT catheter of claim 22, further comprising:
- a closed balloon disposed around the distal portion and being filled with a liquid that is transparent to OCT wavelengths;
- wherein the closed balloon is inflatable against a surface of the interior body.

24. The OCT catheter of claim 22,
wherein the mechanical indenter pin includes an opening along the longitudinal axis of the mechanical indenter pin through which the OCT imaging sensor directs the OCT beam.

* * * * *